Jan. 9, 1973 E. T. GENTILE ET AL Plant Pat. 3,289
CHRYSANTHEMUM PLANT
Filed Dec. 14, 1970
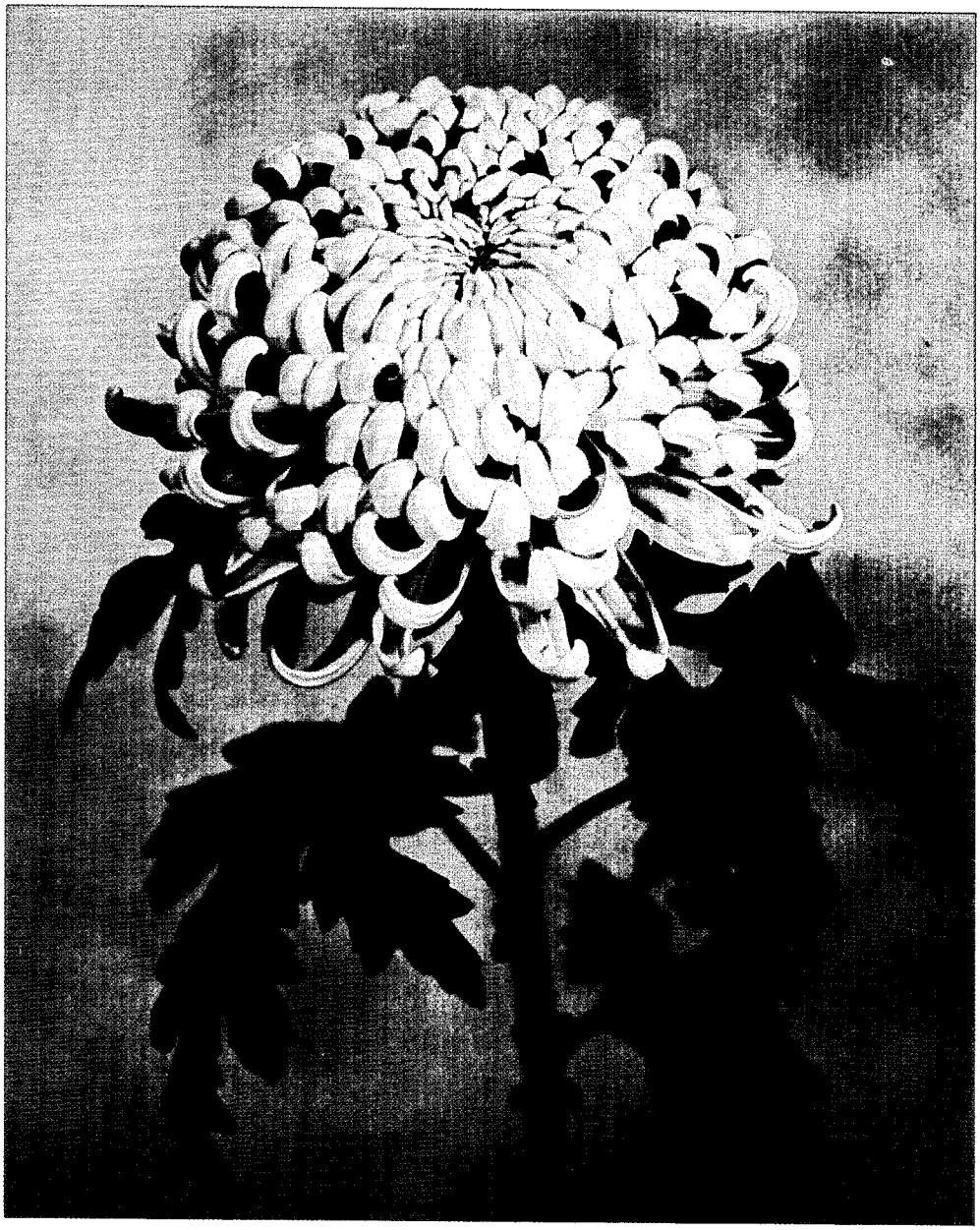

United States Patent Office

Plant Pat. 3,289

Patented Jan. 9, 1973

3,289
CHRYSANTHEMUM PLANT

Eugene T. Gentile, Reading, Mass., and Walter H. Jessel, Jr., Doylestown, and William E. Duffett, Akron, Ohio, assignors to Yoder Brothers, Inc., Barberton, Ohio

Filed Dec. 14, 1970, Ser. No. 98,217

Int. Cl. A01h *5/00*

U.S. Cl. Plt.—80 1 Claim

The present invention comprises a new and distinct cultivar of chrysanthemum plant which is a sport of the unpatented cultivar Pink Mefo, which is no longer commercially available in the trade.

The new cultivar is similar in many respects to Mefo, which is white and the parent variety of the entire Mefo family, which has enjoyed substantial commercial success in the United States, having the same characteristics as Mefo of:

(1) Foliage shape.
(2) Flower form.
(3) Foliage color.
(4) Ivory white color when finished under the higher light, higher temperature conditions of early fall, late spring and summer when night temperatures exceed 60° F. and day temperatures exceed 68–70° F.

The cultivar is distinguished from Mefo by the following characteristics:

(1) ½″ smaller flower with better form retention.
(2) A much darker pink color when flowered under the lower light, lower temperature conditions of late fall through early spring, when night temperatures do not exceed 60° F. and/or day temperatures seldom go above 68–70° F.
(3) 3″ less vigor.
(4) Slightly smaller foliage.
(5) 3–5 days later response.

The new cultivar was discovered as a flowering plant in Reading, Mass., and was asexually reproduced by cuttings at Barberton, Ohio. The new cultivar has been found to retain its distinctive characteristics through successive propagations.

The new cultivar when grown in the vicinity of Barberton, Ohio, has a response period of approximately 11 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States and coastal California is from mid-November through April.

The accompanying drawing shows the unique characteristics of the new cultivar, the color being as nearly true as possible with color illustrations of this type.

In the description which follows, color references are to the Munsell Color Book, 1963 edition, and comparison made with the cultivar Mefo.

| Botanical Classification: *Chrysanthemum morifolium* | Improved Pink Mefo | Mefo |
|---|---|---|
| Bloom: | | |
| Size | 4¾″ | 5″. |
| Fully expanded | 5″ | 5½″. |
| Borne | Singly on disbudded plant. | Singly on disbudded plants. |
| Stems | Strong | Strong. |
| Form | Incurve | Incurve. |
| Permanence | 7–10 days | 7–10 days. |

The following color readings for Improved Pink Mefo are based upon flowerings made in Barberton, Ohio, from mid-November through April and only when greenhouse night temperatures are approximately 60° F. and greenhouse day temperatures seldom exceed 68–70° F.

| | Improved Pink Mefo | Mefo |
|---|---|---|
| Bloom (color): | | |
| Center of flower | Dark lavender, 10P6/6 to light lavender, 10P7/6. | Pale yellow, 10Y9/4. |
| Base of petals | Ivory white, 5Y9/1 | Ivory white, 5Y9/1. |
| Inside of petals | Dark lavender, 10P5/4 to lavender, 10P6/4 over ivory white, 5Y9/1. | Ivory white, 5Y9/1. |
| Reverse of petals | Light lavender, 10P8/4 to pale lavender, 10P9/2. | Ivory white, 5Y9/1. |
| Tonality from a distance. | Lavender pink | Ivory white. |
| Discoloration | Ivory white, 5Y9/1 | Ivory white, 5Y9/1. |

Improved Pink Mefo

Petals:
*Texture.*—Smooth.
*Appearance and form.*—Open at base, broad ridged keel tapering to a hooded point.
*Arrangement.*—Composite, whorled on a single receptacle.
*Persistence.*—Resist shatter.
*Fragrance.*—Typical chrysanthemum.

Reproductive organs:
*Stamen, anthers.*—0–15.
*Pollen.*—None to scant.
*Arrangement.*—Clustered in center of flower, if present.
*Styles.*—Present both ray and disc florets.
*Length.*—Short.
*Ovaries.*—At the base of petal attached to receptacle.

Plant:
*Form.*—Herbaceous.
*Growth.*—Upright.
*Height.*—37″, depending on culture (by way of contrast, Mefo has a height of 40″, depending on culture).
*Spread.*—Very little when grown pinched to none when grown single stem.

Foliage:
*Top side.*—Dark green, 10GY¾.
*Size.*—6″ long, 2⅞″ wide (Mefo is 6½″ long, 3¼″ wide).
*Quantity.*—Numerous.
*Shape.*—Spatulate lobed.
*Texture.*—Smooth.
*Ribs and veins.*—Very prominent.
*Edge.*—Deeply indented.
*Serration.*—Coarse.
*Underside.*—Light green, 7.5GY5/4.
*Stipules.*—Small.

We claim:

1. A new and distinct cultivar of chrysanthemum characterized particularly as to its uniqueness when compared to the cultivar Mefo by its ½″ smaller flower with better form retention, much darker pink color when flowered under the lower light, lower temperature conditions of late fall through early spring when night temperatures do not exceed 60° F. and/or day temperatures seldom go above 68–70° F., 3″ less vigor, slightly smaller foliage, and 3–5 days later response.

No references cited.

ROBERT BAGWILL, Primary Examiner